(12) United States Patent
Ni et al.

(10) Patent No.: US 8,638,099 B2
(45) Date of Patent: Jan. 28, 2014

(54) METHOD FOR REDUCING MAGNETIC RESONANCE TEMPERATURE MEASUREMENT ERRORS IN A MAGNETIC RESONANCE MONITORED HIFU TREATMENT

(75) Inventors: Cheng Ni, Shenzhen (CN); Xiao Dong Zhou, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 272 days.

(21) Appl. No.: 13/118,794

(22) Filed: May 31, 2011

(65) Prior Publication Data
US 2011/0291654 A1 Dec. 1, 2011

(30) Foreign Application Priority Data
May 31, 2010 (CN) .......................... 2010 1 0192723

(51) Int. Cl.
*G01R 33/48* (2006.01)
*A61N 7/00* (2006.01)

(52) U.S. Cl.
USPC .......................................... 324/315; 324/307

(58) Field of Classification Search
USPC .......................... 324/300–322; 600/407–435; 382/128–131
See application file for complete search history.

(56) References Cited

U.S. PATENT DOCUMENTS

| | | | |
|---|---|---|---|
| 5,291,890 A * | 3/1994 | Cline et al. .................. 600/411 |
| 6,128,522 A * | 10/2000 | Acker et al. .................. 600/411 |
| 6,374,132 B1 * | 4/2002 | Acker et al. .................. 600/411 |
| 6,516,211 B1 * | 2/2003 | Acker et al. .................. 600/411 |
| 6,559,644 B2 * | 5/2003 | Froundlich et al. .......... 324/315 |
| 6,773,408 B1 * | 8/2004 | Acker et al. .................. 601/2 |
| 7,542,793 B2 * | 6/2009 | Wu et al. .................... 600/412 |
| 7,956,613 B2 * | 6/2011 | Wald ............................ 324/309 |
| 8,376,946 B2 * | 2/2013 | Littrup et al. ............... 600/437 |
| 8,401,614 B2 * | 3/2013 | Zhou et al. .................. 600/412 |
| 2004/0027127 A1 * | 2/2004 | Mills ............................ 324/317 |
| 2004/0030227 A1 * | 2/2004 | Littrup et al. ............... 600/300 |
| 2004/0039280 A1 * | 2/2004 | Wu et al. .................... 600/412 |
| 2009/0088623 A1 | 4/2009 | Vortman et al. |
| 2009/0096450 A1 | 4/2009 | Roland |
| 2010/0217114 A1 * | 8/2010 | Zhou et al. .................. 600/411 |
| 2011/0248714 A1 * | 10/2011 | Salomir et al. ............... 324/309 |
| 2011/0270075 A1 * | 11/2011 | Vitek et al. .................. 600/411 |
| 2011/0270136 A1 * | 11/2011 | Vitek et al. .................. 601/2 |
| 2011/0291654 A1 * | 12/2011 | Ni et al. ...................... 324/315 |
| 2012/0065494 A1 * | 3/2012 | Gertner et al. ............... 600/411 |
| 2012/0141381 A1 * | 6/2012 | Dewhirst et al. ............ 424/9.321 |
| 2012/0209257 A1 * | 8/2012 | van der Weide et al. ....... 606/23 |

FOREIGN PATENT DOCUMENTS

CN 101273889 A 10/2008

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

A method for reducing magnetic resonance temperature measurement errors, which is used for the high-intensity focused ultrasound device for monitoring magnetic resonance imaging includes obtaining a magnetic resonance phase diagram as a reference image before the high-intensity focused ultrasound device heats the heating area; obtaining another magnetic resonance phase diagram as a heating image during or after the heating process of the high intensity focused ultrasound device; calculating the temperature changes in the heating area according to said heating image and reference image. The method further includes measuring the magnetic field changes caused by the position changes of the ultrasonic transducer of said high-intensity focused ultrasound device, and then compensating for the temperature changes according to said magnetic field changes. The present invention can significantly reduce the temperature errors caused by the position changes of the ultrasonic transducer.

6 Claims, 1 Drawing Sheet

METHOD FOR REDUCING MAGNETIC RESONANCE TEMPERATURE MEASUREMENT ERRORS IN A MAGNETIC RESONANCE MONITORED HIFU TREATMENT

BACKGROUND OF THE INVENTION

1. Field of the Invention

The present invention relates to the high-intensity focused ultrasound (HIFU) field for magnetic resonance imaging (MRI) monitoring, and more particularly to a method for reducing temperature measurement errors of the HIFU device for MRI monitoring.

2. Description of the Prior Art

The Magnetic Resonance (MR) Proton Resonance Frequency (PRF) temperature measurement method can be used to monitor the temperature changes of the HIFU heating part in the HIFU device for MRI monitoring, and its principle is to use the phenomenon that the resonance frequency of protons in water will drift as the temperature changes. The PRF temperature measurement method requires the generation of one benchmark image (MR phase diagram), also known as reference image, before the heating process starts. This reference image provides reference phase information, used to perform subtraction from the phase diagram (also known as heating image) obtained during or after the heating process to determine the exact value of the temperature rise in the heating area.

However, in the actual heating process, the position of the ultrasonic transducer (i.e. treating head) may change after collecting one reference image, and the magnetic susceptibility changes caused by the movement of the ultrasonic transducer will result in static magnetic field changes in the focus area of the ultrasonic transducer, causing the heating image subtracted from the reference image to generate an additional phase difference, leading to temperature measurement errors.

Currently, there are two common solutions for reducing temperature errors. One of the solutions can be referred to as the single reference image method. This method limits the movement range of the ultrasonic transducer after collecting the reference image, thereby limiting the temperature errors to an acceptable range. However, the space usage range of one reference image is very small, and the ultrasonic transducer will move in a larger space range during the HIFU treatment process. To measure the temperatures of individual focus positions of the ultrasonic transducer, it is required that the reference images at different positions be collected, which occurs frequently, thus increasing the complexity level of the temperature measurement and the entire treatment time.

The other solution for reducing temperature errors can be referred to as the self reference method, wherein the reference phase diagram is obtained without heating or collecting reference images but by means of an adapted extrapolation method by using the heating image itself. This method can only monitor the temperature changes around the HIFU focus, and it is difficult to monitor the temperature changes outside the focus in actual applications. In addition, the accuracy of adapted extrapolation is related to the complexity level of the phase diagram and the size of the heating area, so it is difficult to obtain stable, consistent and accurate results in the application.

Moreover, in Chinese patent application No. 200910004957.2, corresponding to U.S. Pat. No. 8,491,614, a method is disclosed for reducing MR temperature measurement errors, which includes: obtaining an MR phase diagram as a reference image before the HIFU device heats the heating area; obtaining another MR phase diagram as a heating image during or after the heating process of the HIFU device; calculating the temperature changes in the heating area according to said heating image and reference image; and which further includes: compensating for said temperature changes according to the magnetic field changes caused by the position changes of the ultrasonic transducer of the HIFU device.

SUMMARY OF THE INVENTION

An object of the present invention is to provide a method for reducing MR temperature measurement errors, so as to accurately measure the temperature changes in the heating area.

The present invention provides a method for reducing MR temperature measurement errors, which is used for the HIFU device for MRI monitoring, and which includes: obtaining a magnetic resonance phase diagram as a reference image before the high-intensity focused ultrasound device heats the heating area; obtaining another magnetic resonance phase diagram as a heating image during or after the heating process of the high-intensity focused ultrasound device; calculating the temperature changes of the heating area according to said heating image and the reference image; and which further includes: measuring the magnetic field changes caused by the position changes of the ultrasonic transducer of said HIFU device, and then compensating for said temperature changes according to said magnetic field changes.

According to an embodiment of the above technical solution, compensating for said temperature changes is based on the following formula, $$\Delta T = \Delta T_{conv} - \frac{\gamma \cdot [\Delta B_{t(r2)} - \Delta B_{t(r1)}] \cdot T_E}{\gamma \cdot B_0 \cdot \alpha \cdot T_E}$$

wherein $\Delta T$ is the temperature change value after compensation, $\Delta T_{conv}$ is the temperature change value calculated according to said heating image and reference image, $[\Delta B_{t(r2)} - \Delta B_{t(r1)}]$ is the magnetic field change caused by the position change from position r1 to position r2 of said ultrasonic transducer, $\gamma$ is the gyromagnetic ratio of the hydrogen atomic nucleus, $B_0$ is the static magnetic field intensity, and $\alpha$ is the proton temperature frequency coefficient.

Measurement of magnetic field changes includes: measuring the phase diagram when said ultrasonic transducer is at the start position; measuring the phase diagrams when the ultrasonic transducer is at different grid points after it moves; calculating the magnetic field changes caused by the movement of the ultrasonic transducer from the start position to different grid points.

The method of the invention further includes: after calculating the magnetic field changes caused by the ultrasonic transducer moving from the start position to a grid point, calculating the magnetic field change caused by the movement of the ultrasonic transducer to another grid point symmetrical to this point relative to the start position.

According to an embodiment, the magnetic field change caused by the movement of the ultrasonic transducer to the other grid point is:

$$\Delta B_{t(-m,-n,-p)}(x,y,z) = -\Delta B_{t(m,n,p)}(x+a^*m, y+b^*n, z+c^*p)$$

wherein $\Delta B_{t(m,n,p)}$ is the magnetic field change caused by the movement of said ultrasonic transducer to the one grid point (m,n,p), $\Delta B_{t(-m,-n,-p)}$ is the magnetic field change caused by the movement of the ultrasonic transducer to another symmetrical grid point (−m,−n,−p), x, y and z are coordinates, and a, b and c are the spaces between the adjacent grid points in the x, y and z directions, respectively.

According to an embodiment, the method of the invention further includes: saving the magnetic field changes; reading the magnetic field when compensating for the temperature changes.

According to an embodiment, the method of the invention further includes: when the ultrasonic transducer is not at the grid point, selecting the grid point closest to the ultrasonic transducer, and using the magnetic field change caused by movement of the ultrasonic transducer to this grid point to compensate for the temperature change.

The integer in each axis closest to the ultrasonic transducer's coordinate after it moves is taken to form the coordinate of the nearest grid point. That is, selecting the grid point ([x/a],[y/b],[z/c]) as the grid point closest to the ultrasonic transducer, wherein [ ] is the function for taking the closest integers.

The ultrasonic transducer has parts that move together with it; during measurement of the magnetic field changes, the magnetic field changes caused by the position changes of the ultrasonic transducer and the parts are measured as a whole.

The present invention thus compensates for the temperature measurement according to the magnetic field caused by the ultrasonic transducer, and the temperature errors caused by position changes of the ultrasonic transducer can be significantly reduced. Compared with the existing single reference image method, the method of the invention does not require frequent collection of reference images at different positions of the ultrasonic transducer, which reduces the complexity level of the temperature measurement and speeds up the whole treatment process. Compared with the existing self-reference method, this invention can accurately measure the temperature changes of the heating area, to provide stable temperature measurement results. Compared with Chinese patent application No. 200910004957.2 as mentioned above, this invention measures the magnetic field changes caused by movement of the ultrasonic transducer to different positions, and will have a broader range of use.

DESCRIPTION OF THE PREFERRED EMBODIMENTS

In order to further explain the purpose, technical solution and advantages of the present invention, the following will further describe the present invention by using embodiments.

Figure 1:
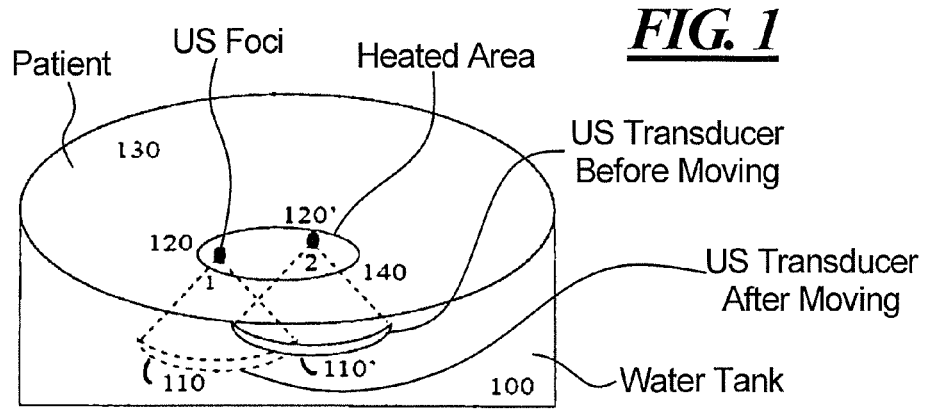
FIG. 1 is a schematic diagram of the position movement of the ultrasonic transducer in an embodiment of the invention.
Figure 2:
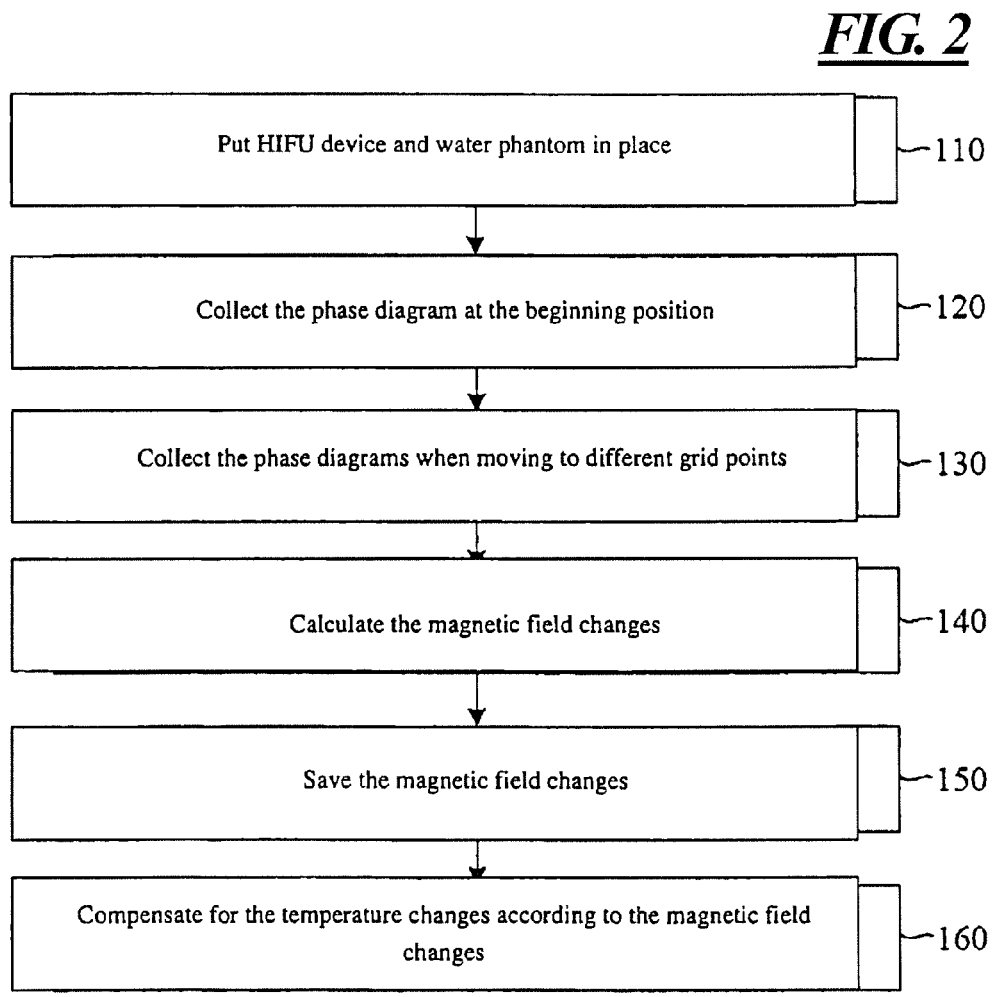
FIG. 2 is a schematic diagram showing the flow of the method according to an embodiment of the present invention.

In FIG. 1, 100 is the water tank, 110 and 110' are the ultrasonic (US) transducer before and after moving respectively, 120 and 120' are the corresponding focuses of 110 and 110' respectively, 130 is the patient's body, and 140 is the heating area of the HIFU device, such as a tumor.

The MR phase diagram is measured by using the gradient echo sequence, and the proton resonance frequency will change as the local temperature changes in the measured tissue, resulting in changes in the PRF, and the PRF changes can be reflected in the MR phase diagram. Therefore, the temperature change can be represented as:

$$\Delta T = \frac{\Delta \varphi}{\gamma \cdot B_0 \cdot \alpha \cdot T_E} \quad (1)$$

wherein $\Delta T$ is the temperature change, $\gamma$ is the gyromagnetic ratio of the hydrogen atomic nucleus ($42.58 \times 10^6$ Hz/T for proton), $B_0$ is the static magnetic field intensity, $T_E$ is the echo time, $\alpha$ is the proton temperature frequency factor, and $\Delta \varphi$ is the phase difference before and after the ultrasonic transducer of the HIFU device releasing ultrasonic energy (heating), i.e.:

$$\Delta \varphi = \varphi_T - \varphi_R \quad (2)$$

In Formula (2), the phase diagram $\varphi_R$ (reference image) is obtained before the heating process of the HIFU device, and the phase diagram $\varphi_T$ (heating image) is obtained during or after the heating process of the HIFU device.

Ideally, the magnetic field of the MRI device is a uniform field in the imaging volume, but there is inherent inhomogeneous field distribution $\Delta B_C$ in the actual magnetic field B, so the actual magnetic field B is:

$$B(x,y,z) = B_0 + \Delta B_C(x,y,z) \quad (3)$$

In the HIFU device for MRI monitoring, the ultrasonic transducer may also introduce an additional magnetic field $\Delta B_t$ into the existing magnetic field. There is no nonlinear magnetic substance such as ferromagnetic material in the MRI imaging area, so the space distribution of $\Delta B_t$ is constant relative to the ultrasonic transducer in the case that the ultrasonic transducer moves laterally or rotates in the direction of $B_0$. If using $\Delta B_t(x,y,z)$ to indicate the magnetic field caused when the ultrasonic transducer is at the position $r=(x,y,z)$, using $\Delta B_t(x',y',z')$ to indicate the magnetic field caused when the ultrasonic transducer moves laterally only without rotating, then $\Delta B_{t(r)}(x,y,z)$ is the translation of $\Delta B_t(x',y',z')$, which can be calculated by the following formula:

$$\Delta B_{t(r)}(x,y,z) = \Delta B_t(x-a, y-b, z-c) \quad (4)$$

As shown in FIG. 1, when the ultrasonic transducer is at position 1 (i.e. the position of the ultrasonic transducer 110), $r1=(x_1,y_1,z_1)$, the magnetic field at this time can be represented as:

$$B_R(x,y,z) = B_0 + \Delta B_c(x,y,z) + \Delta B_{t(r1)}(x,y,z) \quad (5)$$

Obtaining one MR phase diagram at position 1 as a reference image, the phase diagram measured at this time can be represented as:

$$\varphi_R = \gamma \cdot B_{R1} \cdot T_E \quad (6)$$

When the ultrasonic transducer moves to position 2 (i.e. the position of the ultrasonic transducer 110') during or after heating, $r2=(x_2,y_2,z_2)$, the magnetic field at this time can be represented as:

$$B_{r2}(x,y,z) = B_0 + \Delta B_c(x,y,z) + \Delta B_{t(r2)}(x,y,z) \quad (7)$$

Obtaining one MR phase diagram at position 2 as a heating image, the phase diagram obtained at this time can be represented as:

$$\varphi_T = \gamma \cdot (B_{r2} + B_{r2} \cdot \alpha \cdot \Delta T) \cdot T_E \quad (8)$$

wherein $\Delta T$ is the temperature change value in the heating area.

According to Formulae (5) to (8), we can obtain:

$$\Delta T = \frac{(\varphi_T - \varphi_R)}{\gamma \cdot B_{r2} \cdot \alpha \cdot T_E} - \frac{\gamma \cdot [\Delta B_{t(r2)} - \Delta B_{t(r1)}] \cdot T_E}{\gamma \cdot B_{r2} \cdot \alpha \cdot T_E} \quad (9)$$

In the Formula (9), the first term is the temperature change value $\Delta T_{conv}$ obtained by calculating the difference between the phase diagrams, and is equivalent to the temperature change value obtained through the conventional PRF temperature measurement method. The second term is the temperature errors caused by the magnetic field changes $\Delta B_{pos}$ ($=\Delta B_{t(r2)} - \Delta B_{t(r1)}$) due to position changes of the ultrasonic transducer.

In actual application, because $\Delta B_c$ is only several PPM of $B_0$ in magnitude, the effect $\Delta B_t$ on $B_0$ can be ignored, and the $B_{r2}$ in the Formula (9) can be replaced with $B_0$. Therefore, the Formula (9) can be transformed into:

$$\Delta T = \Delta T_{conv} - \frac{\gamma \cdot [\Delta B_{t(r2)} - \Delta B_{t(r1)}] \cdot T_E}{\gamma \cdot B_0 \cdot \alpha \cdot T_E} \quad (10)$$

The magnetic field changes $\Delta B_t$ caused by position changes of the ultrasonic transducer can be obtained by numerical calculation, or can be obtained by measurement in a test. This invention provides an approach different from Chinese patent application No. 200910004957.2 in measurement of the magnetic field changes caused by the position changes of the ultrasonic transducer, to obtain a more accurate temperature value of the heating area.

The space of the heating area is shown as a 3D grid point array, (m,n,p), wherein m, n, p are integers, and correspond to x, y, z directions, respectively, and the spaces between the adjacent grid points in x, y, z directions are a, b, c. For easy description and understanding, the start position of the ultrasonic transducer is marked as (0,0,0) in this embodiment.

The method in this embodiment includes the following steps: Step 110, put the HIFU device into the MRI device with the HIFU device at working position. Place a large water phantom in the MRI device so that the water Phantom covers the treating area.

Step 120, move the ultrasonic transducer to the start position (0,0,0), and collect one phase diagram using the gradient echo sequence, and mark the magnetic field when the ultrasonic transducer is at the start position as σ(0,0,0).

When acquiring the phase diagram, make the imaging plane of the MRI device passing through the ultrasound the focus of the ultrasonic transducer, i.e. keeping the azimuth of the imaging plane in line with the azimuth of the plane used during ultrasound treatment.

Step 130, move the ultrasonic transducer to different grid points, and collect the phase diagrams when the ultrasonic transducer is at different grid points using the gradient echo sequence, and mark them respectively as φ(m,n,p), wherein m, n, p are integers. Also, when collecting the phase diagram, keep the azimuth of the imaging plane of the MRI device in line with the azimuth of the plane used during ultrasound treatment.

Step 140, calculate the magnetic field change $\Delta B_t(m,n,p)$ caused by the movement of the ultrasonic transducer using the Formula (11), i.e. the magnetic field change $\Delta B_t(m,n,p)$ after the ultrasonic transducer moves from the start position (0,0,0) to the grid point (m,n,p).

$$\Delta B_{t,(m,n,p)} = \frac{\varphi(m,n,p) - \varphi(0,0,0)}{\gamma \cdot T_E} \quad (11)$$

Preferably, in Step 130 and Step 140, the magnetic field changes can be calculated without measuring the phase diagrams when the ultrasonic transducer is at each of the grid points, and this embodiment uses the symmetry and the magnetic field changes while the ultrasonic transducer moves to one grid point to calculate the magnetic field change caused by the ultrasonic transducer moving to another grid point symmetrical to this point relative to the start position. The particular calculation according to the symmetry can be seen in Formula (12):

$$\Delta B_{t(-m,-n,-p)}(x,y,z) = -\Delta B_{t(m,n,p)}(x+a^*m, y+b^*n, z+c^*p) \quad (12)$$

wherein $\Delta B_{t(m,n,p)}$ is the magnetic field change caused by the ultrasonic transducer moving to one grid point (m,n,p), $\Delta B_{t(-m,-n,-p)}$ is the magnetic field change caused by the ultrasonic transducer moving to another symmetrical grid point (−m,−n,−p), x, y, z are coordinates, and a, b, c are respectively the spaces between the adjacent grid points in x, y, z directions.

Thus, compared with measurement of the magnetic field changes when the ultrasonic transducer moves to all the grid points, this embodiment can cut down the grid points to be measured by about half, to reduce the measuring time and improve the efficiency of the technical solution of this invention.

In the description above, the technical solution of this invention is described using the example of the ultrasonic transducer moving in a 3D space. The ultrasonic transducer may only move in a 2D plane in specific applications, and those skilled in this field can simplify the operation according to the embodiment above. For example, if the ultrasonic transducer moves only in the XY plane, the Formula (12) can be simplified to become $\Delta B_{t(-m,-n)}(x,y) = -\Delta B_{t(m,n)}(x+a^*m, y+b^*n)$, wherein $\Delta B_{t(m,n)}$ is the magnetic field change caused by the ultrasonic transducer moving to one grid point (m,n), $\Delta B_{t(-m,-n)}$ is the magnetic field change caused by the ultrasonic transducer moving to another symmetrical grid point (−m,−n), x, y are the coordinates, and a, b are respectively the spacing between the adjacent grid points in the x, y direction.

Step 150, this embodiment can further save the obtained $\Delta B_t(m,n,p)$ in the MRI system, to compensate for the temperature changes measured by MR in the future.

Step 160, compensate for the temperature changes measured in the heating area according to the Formula (10). If Step 150 is performed to save the magnetic field changes, then the saved magnetic field changes can be read in this step, to compensate for the temperature changes measured in the heating area.

Moreover, in the actual HIFU operation, if the movement of the ultrasonic transducer is continuous, the ultrasonic transducer may not be at the grid points. In this case, a grid point nearest to the ultrasonic transducer can be selected, and the magnetic field change, when the ultrasonic transducer moves to the nearest grid point, is approximated as the magnetic field change caused by movement of the ultrasonic transducer to the current position. For example, the integer in each axis closest to the ultrasonic transducer's coordinate after it moves is selected to form the coordinate of the nearest grid point. The current position of the ultrasonic transducer can be assumed to be the coordinate (x, y, z), then the grid point nearest to the current position is ([x/a], [y/b], [z/c]), wherein [ ] is the function for taking the closest integers.

if the ultrasonic transducer comprises some parts which move together with it (such as bracket, support etc.), during measurement of magnetic field changes, the embodiment of this invention makes these parts move with the ultrasonic transducer, then the magnetic field changes caused by the movement of these parts can be compensated for at the same time, because the magnetic field changes obtained by the measurement and calculation above, caused when the ultrasonic transducer moves from the start position to different grid points, actually include the magnetic field changes caused by the movement of these parts, that is, during the process of measuring the magnetic field changes, the magnetic field changes caused by the position changes of the ultrasonic transducer and said parts are measured as a whole.

The method of this invention has been verified through particular tests. This invention acquires the phase diagram at the grid points in Z direction, and calculates the magnetic field changes caused by movement of the ultrasonic transducer, wherein the space between the grid points in the Z direction is 1 cm. In this test, the movements of the ultrasonic transducer in the z direction are 0, 10, 20, 30, 40, 50, 60, 70, and 80 mm, respectively. These magnetic field changes, after the ultrasonic transducer moves, are saved, and are used for temperature compensation. From the temperature image before compensation and the temperature image after compensation according to this invention, it can be seen that the temperature errors are significantly reduced.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method of reducing magnetic resonance temperature measurement errors in a treatment of a patient with high-intensity focused ultrasound (HIFU), produced by an ultrasound transducer of a HIFU device, while monitoring said treatment by magnetic resonance (MR) imaging, comprising:

operating an MR data acquisition unit, in which a patient is located in a basic magnetic field generated by the MR data acquisition unit, in order to obtain an MR phase diagram of an area of the patient, as a reference image, with the ultrasound transducer located at a start position in the MR data acquisition unit, before heating the area with HIFU from said ultrasound transducer;

operating said MR data acquisition unit, also with said patient located in said basic magnetic field, in order to obtain a plurality of further MR phase diagrams of said area, as heating images, during or after heating said area with HIFU produced by said ultrasound transducer, while moving said ultrasound transducer to respectively different positions in a grid in said MR data acquisition unit, so that each of said plurality of additional MR phase diagrams is acquired with said ultrasound transducer located at a different one of said positions in said grid;

providing a processor with said reference image and said heating images and, in said processor, automatically calculating, from differences in said MR phase diagrams that form said heating images and from the MR phase diagram that forms said reference image, changes in said basic magnetic field caused by said ultrasound transducer being moved onto said respectively different positions in said grid;

in said processor, also calculating, from differences in said MR phase diagrams that form said heating images with respect to said MR phase diagram that forms said reference image, temperature changes in said area caused by said heating of said area with HIFU; and in said processor, automatically correcting said temperature changes dependent on said changes to said basic magnetic field, thereby producing corrected temperature changes, and making said corrected temperature changes available at an output of said processor in an electronically displayable form.

2. The method as claimed in claim 1, wherein said HIFU device comprises parts which move together with said ultrasonic transducer, and comprising, during measurement of said magnetic field changes, measuring magnetic field changes caused by position changes of the ultrasonic transducer together with said parts as a whole.

3. The method as claimed in claim 1, further comprising, after obtaining the magnetic field changes caused by movement of said ultrasonic transducer from the start position to a grid point, using symmetry in order to calculate the magnetic field changes caused by movement of said ultrasonic transducer to another grid point symmetrical to the grid point relative to the start position.

4. The method as claimed in claim 1, further comprising saving said magnetic field changes after measuring said magnetic changes; and subsequently reading said magnetic field changes when compensating for the temperature changes.

5. The method as claimed in claim 1, further comprising when the ultrasonic transducer is not at said grid point after it moves, choosing a grid point nearest to said ultrasonic transducer, and using the magnetic field changes caused by movement of the ultrasonic transducer onto this grid point in order to compensate for the temperature changes.

6. The method as claimed in claim 5, wherein the integer in each axis closest to the coordinates of the ultrasonic transducer after said ultrasonic transducer moves, is used in order form the coordinates of said nearest grid point.

* * * * *